United States Patent [19]

Knorr et al.

[11] Patent Number: 4,843,167
[45] Date of Patent: Jun. 27, 1989

[54] PROCESS FOR THE PREPARATION OF ORTHO-SUBSTITUTED ARYLCARBOXIMIDOESTERS

[75] Inventors: Harald Knorr, Frankfurt am Main; Gerhard Salbeck, Hofheim am Taunus, both of Fed. Rep. of Germany

[73] Assignee: Hoechst Aktiengesellschaft, Frankfurt am Main, Fed. Rep. of Germany

[21] Appl. No.: 176,794

[22] Filed: Apr. 1, 1988

[30] Foreign Application Priority Data

Apr. 4, 1987 [DE] Fed. Rep. of Germany ....... 3711460

[51] Int. Cl.$^4$ ........................................... C07C 119/20
[52] U.S. Cl. ......................................................... 558/6
[58] Field of Search ............................................ 558/6

[56] References Cited

U.S. PATENT DOCUMENTS 4,102,910 7/1978 Ost et al. .................................. 558/6

FOREIGN PATENT DOCUMENTS 561422   9/1984 Australia ................................. 558/6
0135894  9/1984 European Pat. Off. .................. 558/6
3514450  4/1985 Fed. Rep. of Germany ............ 558/6
862959   4/1986 South Africa ............................ 558/6

OTHER PUBLICATIONS

Robert Roger and Douglas G. Neilson, "The Chemistry of Imidates", Chem. Rev., vol. 61 (1961), 179–211.
P. S. Clezy, A. J. Liepa and N. W. Webb, "The Chemistry of Pyrrolic Compounds", Aust. J. Chem., vol. 25 (1972), pp. 1991–2001.
Lander and Jewson, "Iminoethers Corresponding with Ortho-substituted Benzenoid Amides", J. Chem. Soc., vol. 83 (1903), p. 766.

Bearbeitet von R. dietz, "Ueber Imidoäther des Trimethylencyanids", Chem. Ber., vol. 23 (1890), 2942–2957.

Primary Examiner—John M. Ford
Assistant Examiner—Robert C. Whittenbaugh
Attorney, Agent, or Firm—Curtis, Morris & Safford

[57] ABSTRACT

The present invention describes a process for the preparation of compounds of the formula I

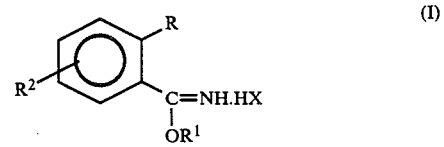

in which
R denotes fluorine, chlorine, bromine or $(C_1-C_4)$alkyl,
$R^1$ denotes $(C_1-C_4)$alkyl,
$R^2$ denotes H, methyl, methoxy, fluorine, chlorine, bromine or trifluoromethyl, and
X denotes Cl or Br, by reaction of nitriles of the formula II

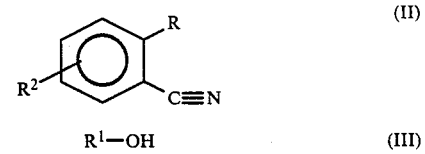

$R^1$—OH  (III)

with alcohols of the formula III and hydrogen chloride or bromide, which comprises carrying out the reaction under pressure at temperatures from − ° C. to +50° C., if appropriate in the presence of a diluent, and subsequently converting the resulting hydrochloride or hydrobromide into the free base.

9 Claims, No Drawings

PROCESS FOR THE PREPARATION OF ORTHO-SUBSTITUTED ARYLCARBOXIMIDOESTERS

Arylcarboximido-esters are used as starting materials for N-carbamylarylcarboximido-esters which are used as agents for combating pests (EP-A-0,135,894).

The preparation of arylcarboximido-ester hydrochlorides by addition of alcohols onto substituted benzonitriles is described in Chem. Rev. 61 (1961) 179. If orthosubstituted benzonitriles are used as the starting substances, however, the desired imido-ester hydrochlorides are obtained in only low yields (J. Austr. Chem. 25 (1972) 1997), or—if 2-chlorobenzonitrile is used, for example—no reaction takes place, see Chem. Rev. 61 (1961) 182-3; and J. Chem. Soc. 83, 766 (1903). If 2-ethoxybenzonitrile is used, according to A. Pinner, Chem. Ber. 23 (1890) 2942, mixtures which cannot be separated are obtained.

According to German Offenlegungsschrift 3,514,450, better results are achieved in the reaction of o-benzonitriles if anhydrous hydrofluoric acid is used instead of HCL. The disadvantage of this procedure is the use of toxic hydrofluoric acid. Stringent safety precautions must be taken when handling this substance. There are also additional disadvantages in that hydrofluoric acid can be handled in combination with alcohols only in quite specific corrosionresistant apparatuses and customary VA steels may not be used.

It is furthermore a disadvantage that excess hydrofluoric acid is used in the process according to German Offenlegungsschrift 3,514,450. Only some of the excess can be eliminated by distillation, so that on subsequent liberation of the imidate by addition of an alkali, significant amounts of fluorides are formed, disposal of which presents problems.

Surprisingly, it has now been found that ortho-substituted arylcarboximido-ester hydrochlorides are obtained directly and in good yields by reaction of ortho-benzonitriles with alcohols and hydrogenchloride or bromide if the reaction is carried out under pressure. The abovementioned disadvantages are thereby avoided.

The invention thus relates to a process for the preparation of compounds of the formula I

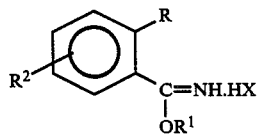
(I)

in which
R denotes fluorine, chlorine, bromine or $(C_1-C_4)$alkyl,
$R^1$ denotes $(C_1-C_4)$alkyl,
$R^2$ denotes H, methyl, methoxy, fluorine, chlorine, bromine of trifluoromethyl, preferably H, and
X denotes Cl or Br, by reaction of nitriles of the formula II

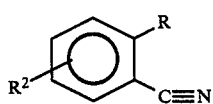
(II)

$$R^1-OH \quad (III)$$

with alcohols of the formula III and hydrogen chloride or bromide, which comprises carrying out the reaction under pressure at temperatures from $-10°$ C. to $+50°$ C., if appropriate in the presence of a diluent, and subsequently coverting the resulting hydrochloride or hydrobromide into the free base.

The reactionn under pressure can also be carried out in the presence of catalytic amounts of chlorides, such as $PCl_5$, $SbCl_5$, $TiCl_4$, $AlCl_3$, $FeCl_3$ or $SnCl_4$, or KI or in the presence of alkali metal sulfides.

Compounds which can be used as the benzonitriles of the formula (II) are, for example, 2-fluorobenzonitrle, 2-chlorobenzonitrle, 2,6-difluorobenzonitrile, 2,6-dichlorobenzonitrile, 2-chloro-4-methylbenzoitrile, 2-bromobenzonitrile and 2-methylbenzonitrile, in particular 2-chloro-, 2-fluoro- and 2,6-difluorobenzonitrile.

Methanol, ethanol, propan-1-ol and propan-2-ol are preferably used as the alcohols of the formula III. The alcohol of the formula III is advantageously used in equivalent amounts or in an excess of up to 50 mol %, based on the nitrile of the formula II. The alcohols of the formula III can moreover also be used as diluents.

The temperature range of the reaction varies, in particular, between 0° C. and 30° C.

Pressure is advantageously understood as the autogenous pressure which develops by forcing in gaseous hydrogen chloride or bromide or by adding liquid hydrogen chloride or bromide. The pressures can vary between 1 and 50 bar, in particular between 3 and 20 bar.

Diluents which can be used are inert compounds, for example hydrocarbons, which may be halogenated, for example heptane, octane, 1,2,2-trifluoro-1,1,2-trichloroethane or methylene chloride, ethers, such as diisopropyl ether, methyl tert.-butyl ether, dioxane or tetrahydrofuran, and aromatics, such as toluene, xylene, chlorobenzene or trifluoromethylbenzene.

The process according to the invention can be carried out by a procedure in which the nitrile of the formula II is taken in the pressure vessel together with the alcohol III, if appropriate in a diluent, and hydrogen chloride or bromide gas is then forced in or liquid hydrogen chloride or bromide is then metered in, with cooling. However, it is also possible to take the nitrile of the formula II and to add hydrogen chloride or bromide in gaseous form or in liquid form and then the particular alcohol III.

To isolate (I), a water-immiscible solvent which dissolves unreacted nitrile is added, if appropriate, to the reaction mixture obtained and the compounds of the formula I are advantageously separated off by extraction with water. The free base of the compounds (I) are then obtained from the hydrochlorides or -bromides by addition of an aqueous base. Suitable bases are alkali metal or alkaline earth metal hydroxides, carbonates or bicarbonates, such as NaOH, KOH, $Na_2CO_3$, $K_2CO_3$, $NaHCO_3$ or $KHCO_3$.

The following examples serve to illustrate the invention in more detail.

EXAMPLE 1

Preparation of 2-chlorophenylcarboximido-ethyl ester 137.6 g of 2-chlorobenzonitrile are taken in 800 ml of ®Frigen 113 (®Frigen 113=1,2,2-trifluoro-1,1,2-trichloroethane) and 50.7 g of dry ethanol in a 4 liter enameled kettle. 511 g of hydrogen chloride gas are forced in at room temperature, with cooling, and the mixture is stirred until about 90% of the 2-chlorobenzonitrile has reacted. The excess hydrogen chloride is released, the contents of the kettle are removed and water is first added, the organic phase is separated off and the solvent is distilled off. The nitrile which remains can be added to the next batch. ®Frigen 113 and a saturated sodium carbonate solution are then added until the pH reaches 8, and the organic phase is separated off. The organic phase is dried, the desiccant is filtered off and the solvent is removed. 175.7 g of 2-chlorophenylcarboximido-ethyl ester remain with a purity of 94%; the product can be further processed directly in this form.

COMPARISON EXAMPLE 137.6 g of 2-chlorobenzonitrile in 800 ml of ®Frigen 113 are taken with 50.7 g of dry ethanol. 365 g of hydrogen chloride gas are passed into the mixture at room temperature, the reaction being carried out under normal pressure. Even after the reaction mixture has been stirred for two days, no noticeable reaction takes place. Working up as described under Example 1 gives 139 g of a solid which consists of 2-chlorobenzonitrile to the extent of 97–98%.

We claim:

1. A process for the preparation of a compound of the formula I

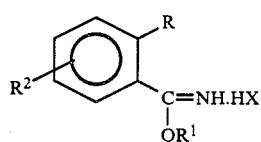

in which
R is fluorine, chlorine, bromine or $(C_1-C_4)$alkyl,
$R^1$ is $(C_1-C_4)$alkyl,
$R^2$ is H, methyl, methoxy, fluorine, chlorine, bromine or trifluoromethyl, and
X is Cl or Br, which process comprises reacting a nitrile of the formula II

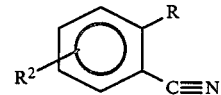

$R^1-OH$         (III)

with an alcohol of the formula III and hydrogen chloride or bromide under pressure at a temperature from $-10°$ C. to $+50°$ C. and subsequently converting the resulting hydrochloride or hydrobromide into the free base.

2. The process as claimed in claim 1, wherein the reaction is carried out at a temperature between 0° C. and 30° C.

3. The process as claimed in claim 1, wherein the reaction is carried out under a pressure of 1 to 50 bar.

4. The process as claimed in claim 1, wherein the reaction is carried out under a pressure of 3 to 20 bar.

5. The process as claimed in claim 1, wherein gaseous hydrogen chloride or bromide is used.

6. The process as claimed in claim 1, wherein liquid hydrogen chloride or bromide is used.

7. The process as claimed in claim 1, wherein hydrogen chloride is used.

8. The process as claimed in claim 1, wherein 2-chloro-, 2-fluoro- or 2,6- difluorobenzonitrile is used as the compound of the formula II.

9. The process as claimed in claim 1, wherein the reaction is carried out in the presence of a diluent.

* * * * *